US006193660B1

(12) United States Patent
Jackson et al.

(10) Patent No.: US 6,193,660 B1
(45) Date of Patent: Feb. 27, 2001

(54) MEDICAL DIAGNOSTIC ULTRASOUND SYSTEM AND METHOD FOR REGION OF INTEREST DETERMINATION

(75) Inventors: John I. Jackson, Menlo Park; Janice L. Marshall, Sunnyvale, both of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/282,602

(22) Filed: Mar. 31, 1999

(51) Int. Cl.$^7$ ........................................... A61B 8/00
(52) U.S. Cl. ..................... 600/443; 600/447; 600/449
(58) Field of Search ........................ 600/437, 440, 600/441, 443, 447, 449, 454, 407

(56) References Cited

U.S. PATENT DOCUMENTS

| 5,419,332 | * | 5/1995 | Sabbah et al. | 600/455 |
| 5,533,510 | * | 7/1996 | Koch, III et al. | 600/443 |
| 5,538,003 | | 7/1996 | Gadonniex et al. | |
| 5,538,004 | * | 7/1996 | Bamber | 600/443 |
| 5,671,739 | * | 9/1997 | Darrow et al. | 600/407 |
| 5,776,063 | * | 7/1998 | Dittrich et al. | 600/408 |
| 5,800,356 | | 9/1998 | Criton et al. | |
| 5,873,830 | | 2/1999 | Hossack et al. | |
| 5,876,342 | * | 3/1999 | Chen et al. | 600/443 |

* cited by examiner

Primary Examiner—Marvin M. Lateef
Assistant Examiner—Ali M. Imam
(74) Attorney, Agent, or Firm—Craig A. Summerfield, Esq.; Brinks Hoter Gilson & Lione

(57) ABSTRACT

A method and system for determining the location of a region of interest throughout a sequence of images is provided. The system, in response to user input or automatically, identifies a region of interest associated with anatomy represented in an image. The data associated with the region of interest is compared with data for other or subsequent images. A maximum degree of correlation between the data associated with the region of interest and data for the subsequent image is determined. A translation and/or rotation associated with the maximum correlation determines the position of a region of interest designator in the subsequent image. The process may be repeated for a plurality of images. The same process may be used to determine the position of the designator in previous images.

38 Claims, 4 Drawing Sheets

MEDICAL DIAGNOSTIC ULTRASOUND SYSTEM AND METHOD FOR REGION OF INTEREST DETERMINATION

BACKGROUND OF THE INVENTION

This invention relates to a medical diagnostic ultrasound system and method for determining the position of a region of interest. In particular, a region of interest in determined in one or more images as a function of a region of interest in another image.

A region of interest may identify particular anatomy in an ultrasound image. As subsequent images are generated, the representation of the anatomy in the image may move. Ultrasound imaging of anatomy is rarely static due to respiration motion, organ motion, transducer motion and other sources of motion. To designate the same anatomy in a plurality of images, the user may manually adjust the position of the region of interest in each image during a review of the images. However, proper placement of the region of interest to identify anatomy in real time is not provided, and manual adjustment may be time consuming.

BRIEF SUMMARY

The present invention is defined by the following claims, and nothing in this section should be taken as a limitation on those claims. By way of introduction, the preferred embodiment described below includes a method and system for determining the location of a region of interest throughout a sequence of images. The system, in response to user input or automatically, identifies a region of interest associated with anatomy represented in an image. The data associated with the region of interest is compared with data for other or subsequent images. A maximum correlation between the data associated with the region of interest and data for the subsequent image is determined. A translation and/or rotation associated with the maximum correlation determines the position of a region of interest designator in the subsequent image. The same process may be used to determine the position of the designator in previous images.

In one aspect, a method for determining a region of interest with an ultrasound system is provided. A first region of interest associated with a first set of data is identified from a first frame of data. The first set of data is correlated with a second frame of data. A second region of interest in the second frame of data is determined as a function of the correlation. An image that is a function of the second frame of data is displayed, and the second region of interest is designated in the image.

In a second aspect, the first and second frames of data are provided on a display with associated designations of the region of interest. A processor performs the correlation and determination of the position of the regions of interest.

In a third aspect, a method for positioning a region of interest in a sequence of images with an ultrasound system is provided. A sequence of images are displayed. Each image comprises a region of interest designator. The region of interest designator in each one of the sequence of images is positioned as a function of a correlation value.

Further aspects and advantages of the preferred embodiments are discussed below.

DETAILED DESCRIPTION OF THE INVENTION

To determine the position of a region of interest in each image, an anatomical feature, speckle or another feature within a first image is identified. Preferably, an edge or other dominant feature related to an atomical structure represented in the image is identified. The position of the feature in subsequent images is estimated by correlating the data associated with the identified feature in the first image with data associated with subsequent images. The data corresponding to the region of interest is translated and/or rotated to various positions relative to the data used for subsequent images. A translation and/or rotation associated with the highest degree of correlation determines the position of the identified feature in each of the subsequent images. A region of interest designator is positioned in each image as a function of the translation and/or rotation associated with the highest degree of correlation (i.e., to surround or label the identified feature).

Figure 1:
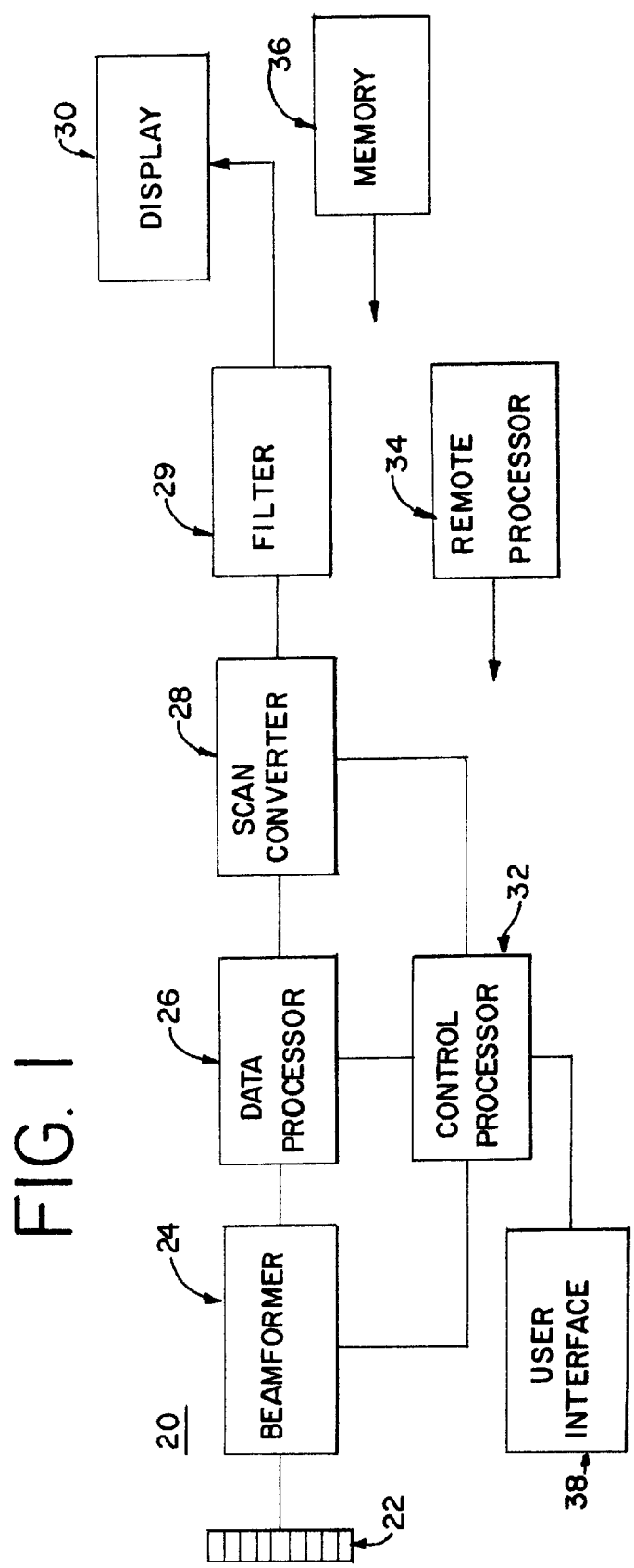
FIG. 1 is a block diagram of an ultrasound system for determining the position of a region of interest.

Referring to FIG. 1, a block diagram of an ultrasound system for determining the position of a region of interest is generally shown at 20. The ultrasound system 20 includes a transducer 22, a beamformer 24, a data processor 26, a scan converter 28, a filter 29, a display 30, a control processor 32, and a user interface 38. The ultrasound system 20 may comprise an 128XP®, Aspen™ or Sequoia® ultrasound system from Acuson Corporation. Other systems may be used, such as systems adapted to process ultrasound data (e.g. the Aegis® system from Acuson Corporation) or systems made by other manufacturers.

Based on control signals from the control processor 32, the beamformer 24 provides excitation signals to the transducer 22. The transducer 22 comprises one of a one-dimensional, two dimensional or 1.5 D transducer. Various elements of the transducer 22 generate focused acoustical waveforms in response to the excitation signals. Based on the control instructions, a region of a patient is scanned in any of various formats, such as curved linear, trapezoidal, sector, Vector®, or linear. Other formats may be used, including formats associated with pulsed wave or continuous wave transmissions or M-mode imaging. Echo signals responsive to the transmitted acoustic waveforms are received by the various elements of the transducer 22. In response, the transducer 22 generates echo signals. The beamformer 24 receives the echo signals and generates in-phase and quadrature data or radio frequency (RF) data. The beamformer 24 may isolate echo signal information at a fundamental transmit frequency band or at a harmonic of the fundamental frequency.

The isolated in-phase and quadrature or RF data is provided to the data processor 26. The data processor 26 comprises a B-mode processor, a Doppler processor, or both the B-mode and the Doppler processor. The B-mode processor envelope detects the in-phase and quadrature data and log compresses the result to generate intensity data. The intensity data may be used for B-mode or M-mode imaging. The Doppler processor generates energy, velocity, or variance data or data representing combinations thereof from the in-phase and quadrature data. The data output from the Doppler processor may be filtered to represent tissue motion, blood flow or combinations thereof. Furthermore, the Doppler processor may output data for a spectral strip display (i.e., data representing a range of frequencies and associated energies as a function of time for one or more locations within the patient).

Data generated by the data processor 26 is scan converted by the scan converter 28 through interpolation or other processes. The scan converter 28 reformats the data from the polar coordinate pattern associated with the scan format to a Cartesian coordinate pattern for display. The scan converted data is provided to the filter 29.

The filter 29 comprises a digital signal processor, a general processor programmed with software or another filtering device. Preferably, a two-dimensional filter with separable axial and azimuthal FIR filters is used. As shown, the filter 29 receives information output by the scan converter 28. In alternative embodiments, the filter 29 is between or within other components of the system 20, such as filtering the output of the image processor 26 prior to scan conversion. In one embodiment, the filter 29 is implemented by the control processor 32 or another processor. The filter 29 filters data for correlation calculations. The filter 29 may also filter data used for generating images on the display 30. In alternative embodiments, the filter 29 is by-passed or not included in the system 20.

The filter 29 spatially filters the ultrasound data output by the scan converter 28. The filter 29 preferably applies low pass filtering to remove fine detail related to pixel quantization. The filter 29 may also high pass filter to remove DC and low frequency variations in the data. In alternative embodiments, the filter 29 comprises a band pass filter. Preferably, the filtering avoids blurring or otherwise reducing edges of anatomy identifiable by the transitions between spatially adjacent data. The output of the filter 29 is provided to the display 30 for generation of an image and/or to a processor for correlation calculations.

The user interface 38 comprises one of a keyboard, dedicated keys, buttons selectable on the display 30, a trackball, a mouse, other user input devices and combinations thereof. The user interface 38 provides user input information to the control processor 32 for operating the system 20. As discussed below, the user interface 38 may also be used in conjunction with the control processor 32 to designate one or more regions of interest on an image.

The control processor 32 comprises a digital signal processor, a general processor, or a combination of processors or other processor. The control processor 32 controls the operation of various components of the ultrasound system 20. In one embodiment, the control processor 32 also processes ultrasound data for determining the position of regions of interest in a sequence of images. As used herein, ultrasound data includes data at intermediate stages within or data input or output from any one or more of the beamformer 24, the data processor 26, the scan converter 28 or the display 30. For example, the control processor has access to data output by the data processor 26 or data output by the scan converter 28. Preferably, the ultrasound data comprises scan converted data. In alternative embodiments, other ultrasound data is used for correlation analysis to determine the position of the regions of interest.

Alternatively or additionally, the ultrasound data is transferred to a remote processor 34, either directly, such as over a network, or indirectly, such as on a removable storage medium. The remote processor 34 comprises a personal computer, a workstation, a motion processor, or other processor for determining the position of regions of interest. For example, the remote processor 34 comprises an AEGIS® workstation system from Acuson Corporation. In yet other alternative embodiments, processors within any of the beamformer 24, data processor 26, scan converter 28 or display 30 determine a correlation between a set of ultrasound data and a frame of ultrasound data.

A memory 36 is associated with the processor for determining the position of regions of interest. The memory 36 is directly connected to the relevant processor or is remote from the processor. The memory 36 comprises a RAM device, VCR, solid state memory, disk drive or other memory device for storing frames of data.

The ultrasound system 20 generates frames of data, each frame of data corresponding to an ultrasound image. As discussed above, each frame of data is in any of various formats, such as the sector format shown in FIGS. 2A–2D. Each datum (i.e., pixel) in a frame of data represents a unique spatial location. For example, a frame of data includes a plurality of B-mode intensities. Each B-mode intensity is associated with an azimuthally positioned scan line and a range along the scan line. The position in the axial and azimuthal dimensions comprises location data. In alternative embodiments, a frame of data and associated image corresponds to M-mode or spectral Doppler data at a particular time.

Preferably, the frames of data are acquired sequentially without any intervening acquisitions. In alternative embodiments, one or more frames of data are acquired in between acquisition of frames of data used for determining the position of a region of interest.

Figure 2A:
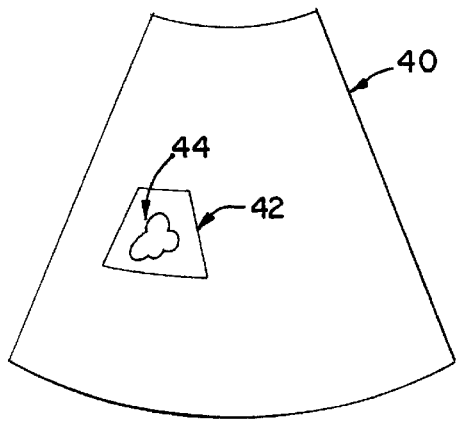
FIGS. 2A–2D represent displays of ultrasound images and associated regions of interest.

A sequence of frames of data are acquired and used to generate a sequence of images. Referring to FIG. 2A, each image 40 includes a region of interest designator 42. In alternative embodiments, only one or fewer than all of the images 40 in the sequence include the designator 42. The region of interest designator 42 identifies anatomic structure represented by the image 40. The region of interest designator 42 comprises an outline box of any various geometric shapes, such as the sector shape shown. The region of interest designator may comprise closed shapes, a set of closed shapes, a single point or gate, a line, a label or other designators of a particular portion of the image 40.

Figure 2B:
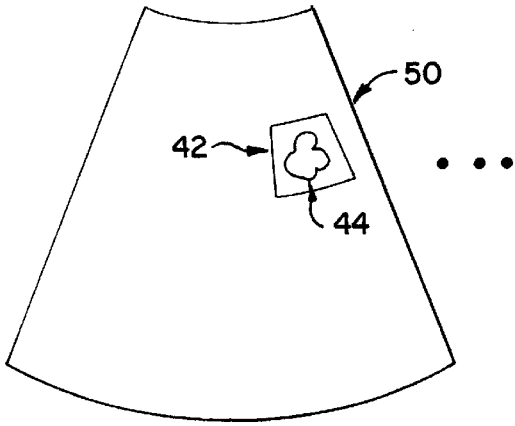
Figure 2C:
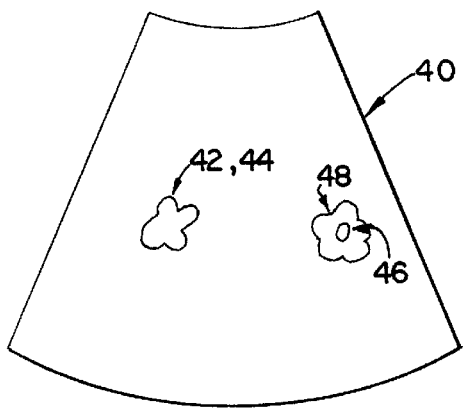

Referring to FIG. 2C, the region of interest designator 42 also comprises an outline box, but is an outline of an anatomical structure 44. A region of interest designator 46 associated with a gate, such as a PW gate, is also shown. More, fewer or different regions of interest and associated regions of interest designators may be used on any image 40.

Figure 3:
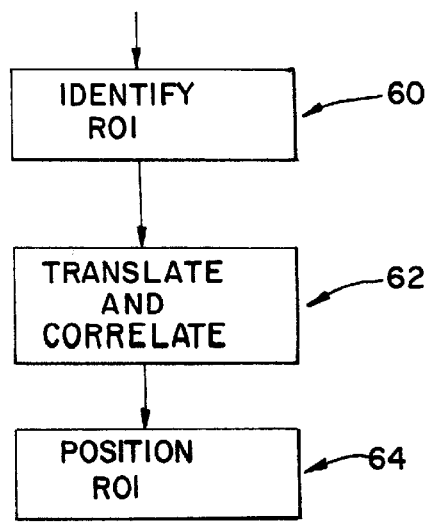
FIG. 3 is a flow chart representing one embodiment of the steps performed for determining the position of a region of interest.

Referring to FIG. 3, a flow chart representing the steps performed for determining the position of a region of interest designator is shown. A region of interest within an image is identified at step 60. In step 62, the region of interest of subsequent images that corresponds to the identified region of interest is determined using translation and correlation. As used herein, translation broadly includes linear translation, rotation and translation with rotation. Regions of interest and associated designators in the subsequent images are positioned in step 64 as a function of the correlation.

The region of interest and associated region of interest designator 42 are identified on one image, such as the first image in a sequence. Later images or more than one image may be used for identifying the region of interest.

In one embodiment, the system 20 automatically determines the region of interest. For example, the control processor 32 or another processor applies an algorithm to data associated with the image, such as detected or scan converted ultrasound data. In one embodiment, the algorithm identifies edges associated with structure boundaries based on intensity or movement differences. For example, the region of interest or associated anatomical feature is preferably identified using one of various metrics, such as gradient, entropy or texture content. For gradient based identification, the location or locations associated with a frame of data corresponding to the maximum gradient or change in ultrasound data amplitude is selected as the feature. For example, a location or locations associated with an edge of an imaged structure is selected. Other selection processes may be used, including selecting a plurality of locations associated with gradient values above a threshold.

In one embodiment, the ultrasound data is convolved with one or more kernels or matrices to generate the gradient data. For example, azimuthal and axial gradient values are determined by using an azimuthal kernel and an axial kernel. In two different embodiments, the kernels are given by [1, −1] and [1, 2, 0, −2, −1]. Any of various kernals may be used, including kernels comprising matrices of any size, such as 3 by 3, 9 by 9 or 9 by 12. Furthermore, the kernel may be derived from a Gaussian or Laplacian of a Gaussian or other functions. Other techniques to identify gradient or change information may be used, such as filters or look-up tables.

To convolve the X or azimuthal gradient, the kernel is aligned with the ultrasound datum of interest within the frame of data, such as aligning the upper left corner of the matrix with the datum. Using the neighboring ultrasound data and the datum of interest, an output gradient is determined by convolution with the kernel. The kernel is repositioned for the next datum of interest. The process is repeated until an X gradient is determined for all or a subset of all the locations represented by the ultrasound data. Likewise, the Y or axial gradient is determined.

For each location within the frame of data, the gradient magnitude is determined from the X and Y gradients. In one embodiment, the gradient magnitude is equal to the absolute value of the X gradient plus the absolute value of the Y gradient. In alternative embodiments, the true magnitude, the square root of the X gradient squared plus the Y gradient squared, is determined. Other gradient magnitude calculations may be used.

In other embodiments, the system 20 identifies the region of interest using one of other algorithms. For example, a threshold is applied to the ultrasound data to identify locations within the region of interest. As another example, artificial intelligence techniques using matched filters to identify a texture shape may be used. The system 20 may adjust any of the regions of interest identified in response user input.

In alternative embodiments, the user designates the region of interest. In response to input from the user interface, the system identifies the region of interest. For example, the user traces the region of interest in a displayed image using a trackball or mouse. The system 20 determines the spatial location of the user trace relative to the frame of data used to create the image. Other user input may be used to designate a region of interest, such as the placement of a cursor for a PW gate or placement and sizing of a two-dimensional designator.

The system 20 determines a set of data from the frame of data used to generate the image that corresponds to the identified region of interest. The set of data comprises a sub-set of the frame of data. For a PW gate, the set of data may comprise a set of one datum. The set of data may correspond to a plurality of regions of interest, such as where the user identifies two or more regions of interest in an image that are to be tracked in subsequent images.

In one embodiment, the set of data is expanded to include data from locations adjacent or near the identified region of interest. Expansion may allow for more accurate correlation by including additional structural information within the set of data. The expansion may include any grouping of locations, such as including five additional spatial locations added to each side of the region of interest. In one embodiment, the expansion includes the addition of spatially separated data, such as adding only every other location for an additional range from one or more sides of the region of interest. In alternative embodiments, the set of data is reduced, such as by selecting every other datum or other sub-set of the set of data corresponding to the region of interest or by selecting data within the set of data corresponding to the region of interest as a function of metric information (e.g., identifying locations adjacent the maximum gradient with gradient values above a threshold). The set of data may be both expanded by adding additional locations and reduced by selecting certain ones of the expanded set of data.

If the region of interest and corresponding set of data represents a PW gate, the set of data is preferably expanded. A region of locations surrounding the PW gate location is included in the set of data, such as a 5 by 5 or other sized and/or shaped region. For a vessel, the preferred region is a square shape that includes the vessel walls and is at least 10 by 10 pixels in size.

Referring to FIG. 3, the region of subsequent images that corresponds to the identified region of interest is determined using translation and correlation in step 62. The control processor 32 or another processor uses the set of data for correlation calculations. The set of ultrasound data is correlated with ultrasound data in a second frame of ultrasound data. The set of ultrasound data is also separately correlated with ultrasound data in any subsequent or previous frames of ultrasound data, such as associated with a sequence of images. In alternative embodiments, different sets of ultrasound data are used for correlation with subsequent or previous frames of data. For example, the identified set of data from a first frame of data is correlated with a second frame of data to determine the position of the region of interest designator relative to the second frame of data. Data from the second frame of data corresponding to the determined region of interest designator is then used as the set of data for correlation with a third frame of data. The set of data from the first frame of data may be used to correlate with more than one subsequent or previous frames of data before being replaced.

The motion of the anatomy associated with the region of interest between the two frames of ultrasound data is estimated as a function of the correlation in step 64. Based on the estimated motion, the position of the region of interest designator 42 relative to each of the frames of data is determined. The identified set of ultrasound data from the first frame of ultrasound data is placed in different relative positions to the second frame of ultrasound data and corresponding correlation values are calculated. Preferably, a cross-correlation or a similar method is used. Such techniques (which will be referred to herein generally as correlation techniques) have been used for tracking blood flow. In one embodiment, a sum of absolute differences (SAD) correlation technique is used.

For each of a plurality of relative positions, a correlation value is determined. The identified set of data is translated and rotated to various positions to determine respective correlation values. If a particular translation and/or rotation results in a SAD that is close to zero, then it is probable that the location of the anatomy in the second frame of ultrasound data has been determined. The translation and rotation required to determine the location of the region of interest indicates the motion of the region between the two respective frames of ultrasound data. In alternative embodiments, the maximum of a cross-correlation is selected as indicating the location of the region of interest.

Translation to different positions for determining correlation preferably corresponds to one or both of axial and azimuthal translation. In one embodiment, the selected ultrasound data and corresponding locations are translated in the azimuthal dimension by ten locations on each side of an origin point and in the axial dimension by ten locations from each side of the origin point. The search range may be a function of time between acoustic frames and the region of the body scanned. The set of ultrasound data is positioned relative to the second frame of ultrasound data at each possible integer location within the seven location range. Therefore, the selected locations and associated ultrasound data are translated to four hundred and forty one different positions. A combination of coarse sampling followed by fine sampling may be used.

The origin point is selected (1) as a location associated with no translation, (2) as a location that is a function of a likely amount of translation based on previous amounts of translation or on the type of anatomy being imaged, (3) as a location that is selected arbitrarily, or (4) as a location selected using any other function.

For each translation position, the selected ultrasound data is rotated by 0.1 degrees over a −2 to 2 degree range. Therefore, for each translation position, 41 rotational positions are provided. For each correlation value associated with a different rotation, ultrasound data is interpolated within the second frame of data to align with the rotated set of ultrasound data and associated locations. In one embodiment, linear interpolation is used, but other interpolation or extrapolation methods may be provided. For each translation and rotation position, a correlation value is calculated. In this embodiment, 18,081 correlation values are determined.

In another embodiment, correlation values are only determined for various translations without any rotation. In other embodiments, different ranges and numbers of positions within the ranges for translations and/or rotations are used, such as determining correlation values for every other location position within a translation range with the same or an unequal number of locations on each side of the origin point.

In other alternative embodiments, past estimates of motion associated with the region of interest or the type of anatomy associated with the region of interest are used to determine the range of translations and rotations and the number of locations within a range on each side of the origin point. For example, if past estimates of motion show an average azimuthal translation of five pixels in one direction, the origin point is selected as a translation of five pixels in the direction of past motion. Additionally or alternatively, the previous estimates of motion are used to select a larger azimuthal translation range, such as twice the range of translation on one side of the original point. Furthermore, previous estimates of motion are used to identify an area for more dense determination of correlation values, such as determining a correlation value every second or third location position for locations representing motion that is opposite previous estimates. Using past estimates to estimate motion may include triggering to estimate cyclical movement associated with a heart or respiration cycle.

After a correlation value is determined for each position associated with translation and/or rotation, the position of the region of interest in the second frame of ultrasound data is selected. The lowest SAD correlation, the highest cross-correlation or another correlation determines the selected position.

Where each image in the sequence of images corresponds to imaging generally the same region of the patient, the region of interest may not move by large amounts from one image to the next. In one preferred embodiment, weights are applied to the various correlation values. Correlation values associated with smaller amounts of movement and/or rotation are emphasized over correlation values associated with larger amounts of movement. For example, SAD correlation values associated with smaller amounts of movement are multiplied by smaller values, and SAD correlation values associated with larger amounts of movement are multiplied by larger values. The least of the weighted correlation values is selected to determine the position of the region of interest. The weights are reversed for cross-correlation correlation values. Any of various weighting functions may be used, including linear and non-linear functions and functions limiting the amount of possible movement of the region of interest between images. If the selected correlation value is associated with movement beyond a threshold value, an error signal may be provided.

Additionally or alternatively, the selected correlation value is compared to a threshold to avoid a region of interest that appears to randomly move between images. If the correlation value is above (i.e. cross-correlation) or below (i.e. SAD) the threshold, the correlation value is used as discussed above to determine the location of the region of interest designator 42. If the selected correlation value does not satisfy the threshold, then (1) an error signal is provided on the display, (2) the region of interest designator 42 is displayed in a previously determined position, (3) the region of interest designator 42 is positioned based on extrapolation from previously determined positions or (4) the region of interest designator 42 is not displayed.

Figure 2D:
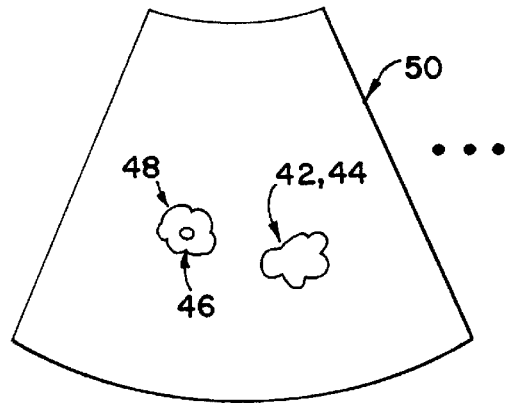

After the position of the region of interest is determined, the region of interest designator 42 may be displayed with the associated image on the display 30. Referring to FIG. 2B, an image 50 generated as a function of the second frame of ultrasound is shown. Based on the correlation, the region of interest designator 42 is displayed at a different position than for the first image 40. The anatomy 44 has correspondingly moved positions within the image 50. While a large translation to the right and a smaller but visible translation up are shown, the translation between any two images may or may not be visibly detectable. The translation throughout a sequence of images is more likely to be detected. Referring to FIG. 2D, the region of interest designators 46 and 42 are displayed with the corresponding anatomy. For the region of interest designator 42 associated with the anatomy outline, the edges of the region of interest designator 42 may be re-determined for each subsequent image 50 where the anatomy may change dimensions or shape. The region of interest designator 42 preferably is the same size as the originally identified region of interest prior to expansion for correlation determination. In alternative embodiments, the region of interest designator 42 represents the expanded region of interest.

For M-mode images, the region of interest designator is repositioned along a line. The translation associated with determining the best correlation is performed only along the relevant scan line.

In one embodiment for two dimensional region of interest designators, the region of interest designator 42 is the same size and shape as displayed throughout the sequence of images. In another embodiment, the region of interest designator 42 changes sizes, such as associated with matching the region of interest to anatomical structure. The region of interest designator 42 may also change sizes as a function of the selected correlation value. If the correlation value is associated with a high degree of correlation, the region of interest designator 42 may be kept the same size. If the correlation value is associated with a small degree of correlation, the region of interest designator 42 is enlarged to more likely include the anatomy of interest.

Figure 4:
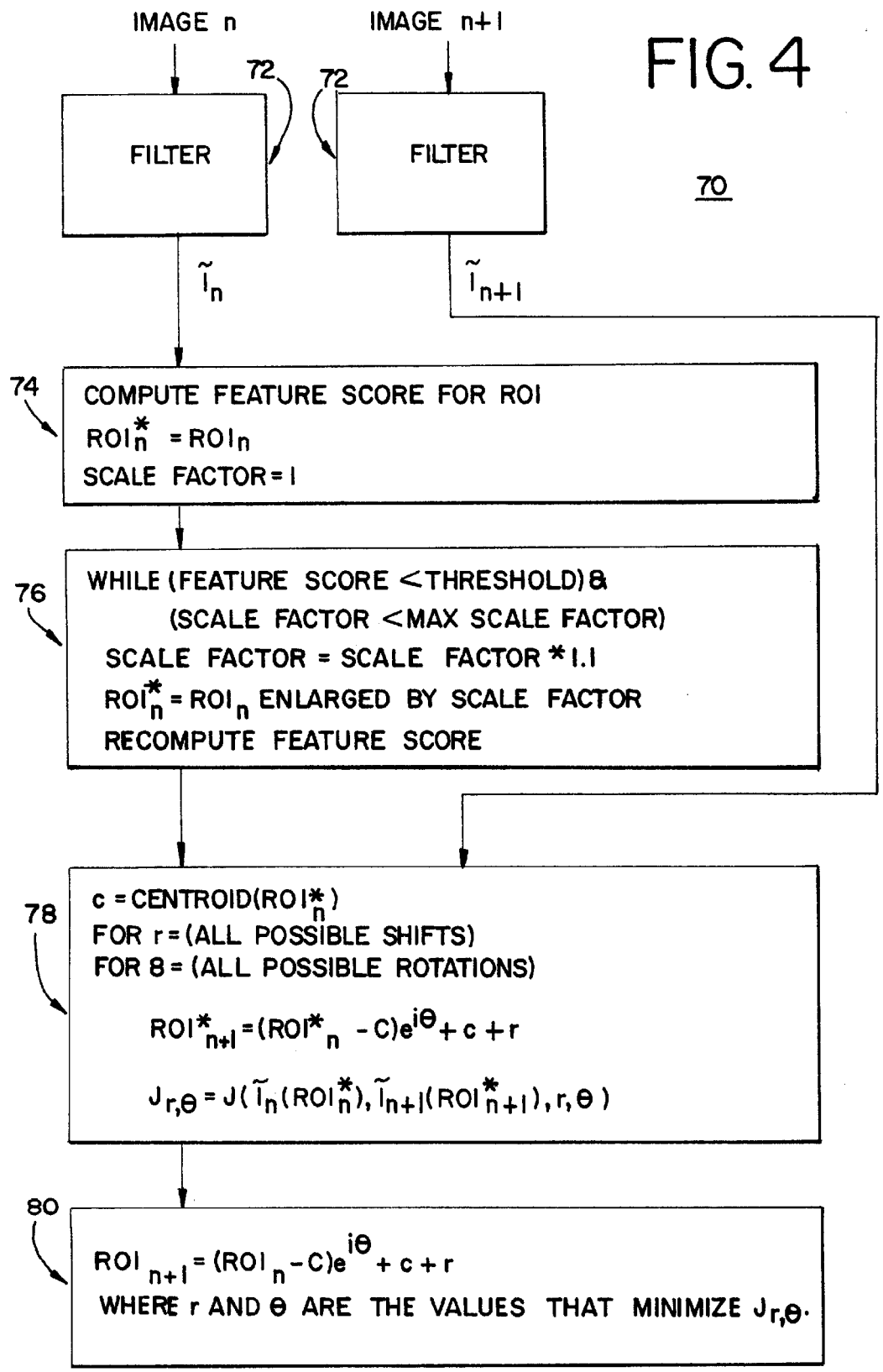
FIG. 4 is a flow chart representing one embodiment of the steps performed for determining the position of a region of interest.

Referring to FIG. 4, a flow chart of one preferred embodiment for positioning a region of interest is shown at 70. In step 72, first (n) and second (n+1) frames of scan converted ultrasound data are filtered, such as the band pass or high and low pass filtering discussed above.

A region of interest and related parameters are identified in the first frame of data at step 74. A variable region of interest, ROI*, is set equal to the identified region of interest, and a scale factor is set to 1. A feature score is calculated from the set of data associated with the region of interest. The feature score may provide an indication that the region of interest includes texture sufficient for correlation. For example, the feature score is the standard deviation in the set of data. As another example, the feature score is the mean value of the set of data. Other indications of texture associated with the region of interest may be used.

In step 76, the region of interest used for correlation is enlarged. The region of interest is enlarged as a function of the feature score and a maximum scale factor. If the feature score is less than a threshold and the maximum scale factor has not yet been reached, the scale factor is increased. In alternative embodiments, the scale factor is increased if the feature score is between two thresholds (e.g., a feature score based on the mean) or greater than the threshold. Various scale factor increases may be used, such as multiplying the scale factor by 1.1 or another value. The variable region of interest is enlarged as a function of the scale factor, such as determining the area and center of the variable region of interest, multiplying the area by the scale factor and determining the locations within the enlarged region of interest covered by the resulting enlarged area centered at the same location. The variable region of interest is set equal to the enlarged region of interest, and the feature score is recomputed. Step 76 is repeated until the feature score meets the threshold or the maximum scale factor is reached. The maximum scale factor may be any one of various values, such as a value associated with enlargement by a factor of 2 or associated with an area that is a percentage of the full image.

In step 78, correlation values associated with translating and rotating the variable region of interest to different positions relative to the second frame of data are determined. The centroid of the variable region of interest is determined. The variable region of interest is rotated in angular steps of θ and translated in steps of r to various positions relative to the second frame of data. This function may be represented by: $ROI^*_{n+1}=(ROI^*_n-c)e^{i\theta}+c+r$. The correlation values are calculated as discussed above, such as using the minimum sum of absolute differences. The calculation of correlation values may be represented as the cost function J: $J_{r,\theta}=J(I_n(ROI^*_n), I_{n+1}(ROI^*_{n+1}), r, \theta)$, where I represents a filtered frame of data.

In step 80, the minimum cost function is used to determine the position of the region of interest in the second frame of data. r and θ that minimize the cost function represent the translation and rotation of the centroid from the first frame of data to the second frame of data. Steps 72 through 80 may be repeated for subsequent frames of data. Alternatively, steps 72 and 78 through 80 are repeated for comparing the variable region of interest determined in steps 74 and 76 with multiple frames of data.

Ultrasound data associated with the region of interest or the region of interest designator 42 is used for one or more of various purposes. The region of interest designator 42 may be displayed throughout a sequence of images to assist qualitative assessment of an anatomical region. For example, the region of interest designator 42 is used to provide convenient identification of a region during pharmacological intervention or contrast agent injection.

The ultrasound data associated with the region of interest, whether or not the designator 42 is displayed, may be used for quantitative analysis. The ultrasound data comprise data from the second frame of data. The ultrasound data may correspond to an original region of interest before any expansion for correlation, the expanded region of interest, or a region of interest expanded or reduced for quantitative analysis. Various quantities may be calculated. For example, the mean signal intensity or Doppler signal intensity within the region of interest is calculated and displayed. Other quantities that are a function of the area within the region of interest, the translation and/or rotation of the region of interest, the location of the region of interest, data corresponding to the region of interest or other parameters of the region of interest may be calculated. As a sequence of images are displayed, the quantity is calculated for each or a sub-set of the images. A mean of the quantity or other statistical representation of the quantity may be determined and displayed. Additionally or alternatively, a plot of the quantity as a function of time or image number may be displayed or stored. Furthermore, a table of the quantity may be displayed or stored.

Figure 5:
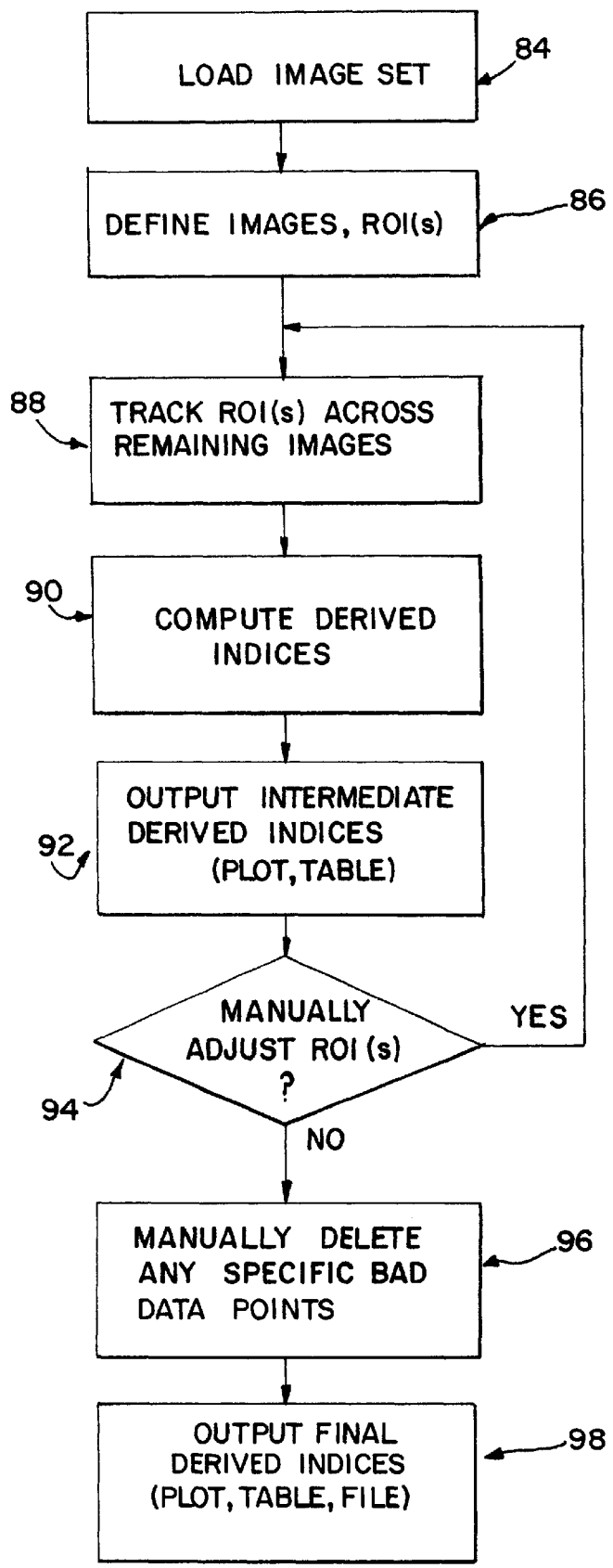
FIG. 5 is a flow chart representing one embodiment of the steps performed for determining indices associated with a region of interest.

Referring to FIG. 5, a flow chart representing one embodiment for deriving one or more quantities as a function of the region of interest tracking is shown. In step 84, a sequence of images are obtained, such as by acquiring the images in real time or by loading the images from a storage device or memory. In step 86, the initial region of interest is identified as discussed above. The first image may correspond to any one of the images within the sequence of images. More than one region may be identified. In step 88, the region of interest is tracked using correlation in other images, such as all other images within the sequence of images. Also as discussed above, the quantity or quantities associated with all, one or a sub-set of all the regions of interest are calculated for each of the images 90. The calculation may be performed in real time as the regions of interest within an image are determined or after the regions of interest for multiple or all the images are determined.

The quantity or quantities are output in step 92. These derived indices may be output in one or more of various forms, such as a plot of the quantity output in real time with the display of the image sequence or as a table of the quantity output after multiple images have been displayed with or without the display of the images.

The user may elect to adjust the region or regions of interest identified in the first image in step 94. After reviewing the quantity or quantities, the user may determine that more accurate or different regions of interest should be identified. If a change is desired, the user causes the system 20 to move or rotate the identified region of interest in the first image, such as by manipulating a trackball. The process returns to step 88 for another determination of the quantity or quantities. The user may also select different quantities for calculation. The process would return to step 90 for calculation of different quantities. If different quantities or regions of interest are not desired, the process continues to step 96.

In step 96, the user may delete any data used for calculation of one or more of the quantities. One or more images may be removed from the sequence, or one of a plurality of regions of interest may be removed. Alternatively, one or more of a plurality of regions of interest are removed from a sub-set, such as one or two, of the images. A sub-set of data within a region of interest may also be removed. In step 98, the output of the quantity or quantities is determined again as a function of the data remaining after step 96. The quantity or quantities may be output in the same or a different format, such as a plot, a table or a file of data.

Another purpose for tracking the region of interest through a plurality of images is the alteration of imaging parameters. Imaging parameters may be altered as a function of the region of interest or the corresponding data. For example, the transmit and receive focal points are adjusted to correspond to the location of a PW gate region of interest. Other imaging parameters may be adjusted, such as the number of focal regions, the number of scan lines, the amount of filtering, the data filtered, the data processed to obtain Doppler information or data stored for later review. For imaging contrast agents, a region associated with transmissions for destroying contrast agents (i.e., high power, longer duration and/or greater bandwidth) may be altered as a function of the tracked region of interest. In this embodiment, other regions of the image are associated with transmissions providing less destruction of contrast agents.

While the invention has been described above by reference to various embodiments, it will be understood that many changes and modifications can be made without departing from the scope of the invention. For example, one dimensional (i.e. M-mode), two-dimensional or three-dimensional regions of interest and associated designators may be tracked through a sequence of images. Different ultrasound systems, whether analog or digital, may be used to acquire and/or display the ultrasound data than are used to determine the location of the region of interest throughout the sequence of images.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A method for determining a region of interest designator with an ultrasound system, the method comprising the steps of:
   (a) identifying a first region of interest associated with a first set of data from a first frame of data;
   (b) correlating the first set of data with a second frame of data;
   (c) determining a second region of interest in the second frame of data as a function of the correlation of step (b);
   (d) displaying an image as a function of the second frame of data; and
   (e) designating the second region of interest in the image.

2. The method of claim 1 further comprising:
   (f) correlating the first set of data with subsequent frames of data;
   (g) determining a subsequent region of interest in each of the subsequent frames of data as a function of the correlations of step (f);
   (h) displaying subsequent images, each subsequent image being a function of one of the subsequent frames of data; and
   (i) designating the subsequent region of interest in each of the subsequent images.

3. The method of claim 1 wherein step (b) comprises calculating a minimum sum of absolute differences.

4. The method of claim 1 wherein step (b) comprises calculating a maximum cross-correlation.

5. The method of claim 1 wherein step (a) comprises identifying the first region of interest in response to a user interface input.

6. The method of claim 5 wherein step (a) comprises identifying the first region of interest as a larger region of interest than designated by the user interface input.

7. The method of claim 1 further comprising:
   (f) inputting a gate location;
   wherein step (a) comprises identifying the first region of interest as a region surrounding the gate location.

8. The method of claim 1 further comprising:
   (f) low pass filtering at least the first set of data and the second frame of data.

9. The method of claim 1 further comprising:
   (f) high pass filtering at least the first set of data and the second frame of data.

10. The method of claim 1 wherein:
    step (b) comprises:
       (b1) translating the first set of data to a plurality of positions relative to the second frame of data;
       (b2) determining a correlation value for each of the plurality of positions; and
    step (c) comprises determining one position from the plurality of positions as a function of the correlation value for each of the plurality of positions.

11. The method of claim 10 further comprising:
    (f) weighting the correlation value for each of the plurality of positions as a function of an amount of translation.

12. The method of claim 1 further comprising step (f) of applying a minimum threshold to the correlation.

13. The method of claim 1:
    wherein step (a) comprises enlarging a selected region of interest, the enlarged region of interest comprising the first region of interest;
    further comprising step (f) of calculating a feature score as a function of the first region of interest;
    wherein step (a) is responsive to the feature score.

14. The method of claim 1 further comprising:
    (f) calculating a quantity as a function of the second region of interest.

15. The system of claim 1 further comprising:
    (f) adjusting a location of a PW gate as a function of a location of the second region of interest.

16. An ultrasound system for determining a region of interest, the system comprising:
    a first display of a first image and a first region of interest, the first region of interest corresponding to a first set of data from a first frame of data, the first image being a function of the first frame of data;

a processor for correlating the first set of data with a second frame of data and for determining a second region of interest in the second frame of data as a function of the correlation; and a second display of a second image and the second region of interest, the second image being a function of the second frame of data.

17. The system of claim 16 further comprising a user interface for identifying the first region of interest.

18. The system of claim 16 further comprising a low pass filter operable to low pass filter at least the first set of data and the second frame of data.

19. The system of claim 16 further comprising a high pass filter operable to high pass filter at least the first set of data and the second frame of data.

20. A method for positioning a region of interest designator in a sequence of images with an ultrasound system, the method of comprising the steps of:

(a) displaying a sequence of images, each image comprising a region of interest designator; and (b) positioning the region of interest designator in each one of the sequence of images as a function of a respective correlation value.

21. The method of claim 20 wherein step (b) comprises positioning the region of interest designator as a function of a minimum sum of absolute differences.

22. The method of claim 20 wherein step (b) comprises positioning the region of interest designator as a function of a maximum cross-correlation.

23. The method of claim 20 further comprising step (c) comprises identifying a first region of interest in a first image in response to a user interface input.

24. The method of claim 23 wherein step (c) comprises identifying the first region of interest as a larger region of interest than designated by the user interface input.

25. The method of claim 23 further comprises step (d) of inputting a gate location; and wherein step (c) comprises identifying the first region of interest as a region surrounding the gate location.

26. The method of claim 20 further comprising:

(c) low pass filtering data for each of the sequence of images.

27. The method of claim 20 further comprising:

(f) high pass filtering data for each of the sequence of images.

28. The method of claim 20 further comprising:

(c) identifying a first region of interest associated with a first set of data from a first frame of data;

(d) translating the first set of data to a plurality of positions relative to each of a sequence of frames of data, each frame of data associated with a respective one of the sequence of images; and (e) determining the correlation value for each of the plurality of positions;

wherein step (b) comprises determining one position of the region of interest designator as a function of the correlation value for each of the plurality of positions for each of the sequence of images.

29. The method of claim 28 further comprising:

(f) weighting the correlation value for each of the plurality of positions as a function of an amount of translation.

30. The method of claim 20 further comprising step (c) of applying a minimum threshold to the correlation value.

31. A method for determining a region of interest with an ultrasound system, the method of comprising the steps of:

(a) identifying a first region of interest associated with a first set of data from a first frame of data;

(b) correlating the first set of data with a second frame of data;

(c) determining a second region of interest in the second frame of data as a function of the correlation of step (b);

(d) calculating a quantity as a function of data from the second frame of data corresponding to the second region of interest.

32. The method of claim 31 further comprising:

(f) correlating the first set of data with subsequent frames of data;

(g) determining a subsequent region of interest in each of the subsequent frames of data as a function of the correlations of step (f);

(h) calculating subsequent quantities, each subsequent quantity being a function of data from one of the subsequent frames of data corresponding to one of the subsequent regions of interest.

33. The method of claim 32 further comprising:

(i) outputting the subsequent quantities;

(j) removing data associated with at least one of the subsequent quantities; and (k) outputting further quantities that are a function of step (j).

34. The method of claim 31 wherein:

step (b) comprises:

(b1) translating the first set of data to a plurality of positions relative to the second frame of data;

(b2) determining a correlation value for each of the plurality of positions; and step (c) comprises determining one position from the plurality of positions as a function of the correlation value for each of the plurality of positions.

35. The method of claim 31 further comprising:

(e) displaying an image as a function of the second frame of data; and (f) designating the second region of interest in the image.

36. The method of claim 31 further comprising:

(e) outputting the quantity;

(f) adjusting the first region of interest; and (g) repeating steps (b), (c) and (d) as a function of the adjustment of step (f).

37. An ultrasound system for determining a region of interest, the system comprising:

a first display of a first image and a first region of interest, the first region of interest corresponding to a first set of data from a first frame of data, the first image being a function of the first frame of data;

a processor for correlating the first set of data with a second frame of data and for determining a second region of interest in the second frame of data as a function of the correlation; and a second display of a quantity, the quantity being a function of data from the second frame of data corresponding to the second region of interest.

38. The system of claim 37 further comprising a user interface for adjusting the first region of interest.

* * * * *